United States Patent
Takahashi et al.

[11] Patent Number: 5,664,937
[45] Date of Patent: Sep. 9, 1997

[54] PRECISELY FLOW-CONTROLLING PUMP

[75] Inventors: Kenichiro Takahashi, Naka-machi; Hironori Kaji, Hitachinaka; Kaoru Hagiya, Hitachi, all of Japan

[73] Assignee: Hitachi, Ltd., Tokyo, Japan

[21] Appl. No.: 382,741

[22] Filed: Feb. 2, 1995

[30] Foreign Application Priority Data

Mar. 2, 1994 [JP] Japan .................. 6-011460

[51] Int. Cl.$^6$ ...................................... F04B 49/00
[52] U.S. Cl. ........................ 417/22; 417/42; 417/44.2; 417/12
[58] Field of Search ...................... 417/17, 18–23, 417/26, 42, 43, 44.2, 12; 210/101, 198.2, 659

[56] References Cited

U.S. PATENT DOCUMENTS

| | | |
|---|---|---|
| 4,137,011 | 1/1979 | Rock ............................ 417/22 |
| 4,233,156 | 11/1980 | Tsukada et al. ............... 210/101 |
| 4,422,942 | 12/1983 | Allington ..................... 210/659 |
| 4,775,481 | 10/1988 | Allington ..................... 417/43 |
| 4,797,207 | 1/1989 | Honganen et al. ............. 210/198.2 |
| 4,832,575 | 5/1989 | Miller et al. .................. 417/22 |
| 4,883,409 | 11/1989 | Strohmeier .................. 417/44.2 |
| 4,981,597 | 1/1991 | Allington et al. ............. 210/656 |
| 5,089,124 | 2/1992 | Mahar et al. ................. 210/198.2 |
| 5,174,472 | 12/1992 | Raque et al. ................. 417/12 |
| 5,253,981 | 10/1993 | Yang et al. ................... 417/22 |

*Primary Examiner*—Timothy Thorpe
*Assistant Examiner*—Xuan M. Thai
*Attorney, Agent, or Firm*—Kenyon & Kenyon

[57] ABSTRACT

In a pump in which dual plunger is reciprocated with cams attached to the rotating shaft of a motor, the delivery pressure of liquid is measured during a certain period in each cycle of the pump. By setting the pressure during the certain period as a standard pressure value, the motor is controlled so that the delivery pressure during the remaining period in each cycle approaches to the standard pressure value. In this pump, rotating-speed-priority control and pressure-priority control are alternatingly performed to decrease pulsation during delivering liquid.

11 Claims, 9 Drawing Sheets

PRECISELY FLOW-CONTROLLING PUMP

BACKGROUND OF THE INVENTION

The present invention relates to a precisely flow-controlling pump used in an analyzing instrument for pumping a liquid specimen with a stable flow rate and, more particularly, to a precisely flow-controlling pump having control flow means used as a pump for a liquid chromatographic apparatus.

In most of pumps used in liquid chromatographic apparatus, the volume inside cylinder is changed by reciprocating a plunger forth and back in the cylinder. Liquid can be always delivered by connecting two pumps in series and independently moving the plungers of the two pumps. The pumps have a structure that liquid is discharged from a delivery port in such a manner that a checking valve attached in a suction port in the cylinder opens when the plunger moves toward a direction to increase the volume inside the cylinder, and the checking valve attached in the suction port in the cylinder closes and a checking valve attached in the delivery port opens when the plunger moves toward a direction to decrease the volume inside the cylinder.

In such pumps, the rotating speed control to drive the cylinders and the geometrical accuracy in the cams converting the rotating movement of the motor into the reciprocal movement of the plungers strongly effect the constancy of delivery flow rate of liquid. As for instable factors, there is malfunction mainly caused by bubbles entering in the liquid or operation lag in the checking valves.

In order to decrease the malfunction, the prior art of compensating pulsating flow by detecting change in delivery liquid pressure is proposed in Japanese Patent Application Laid-Open No. 55-128678 (1980), Japanese Patent Application Laid-Open No. 63-105285 (1988), Japanese Patent Application Laid-Open No. 60-11690 (1985) and Japanese Patent Application Laid-Open No. 58-105028 (1983).

SUMMARY OF THE INVENTION

An object of the present invention is to provide a precisely flow-controlling pump which is capable of performing higher accurate flow control by decreasing the fluctuation in delivery flow rate due to various instable factors of liquid delivery flow rate in conventional pumps.

Describing further in detail, the object of the present invention is to provide a precisely flow-controlling pump in which flow control is performed depending on each of the various causes producing pulsating flow.

BRIEF DESCRIPTION OF THE DRAWINGS

Accompanying drawings will be explained in order to help understanding the present invention, the objects and the features of the present invention other than described above.

DESCRIPTION OF THE PREFERRED EMBODIMENTS

Figure 1:
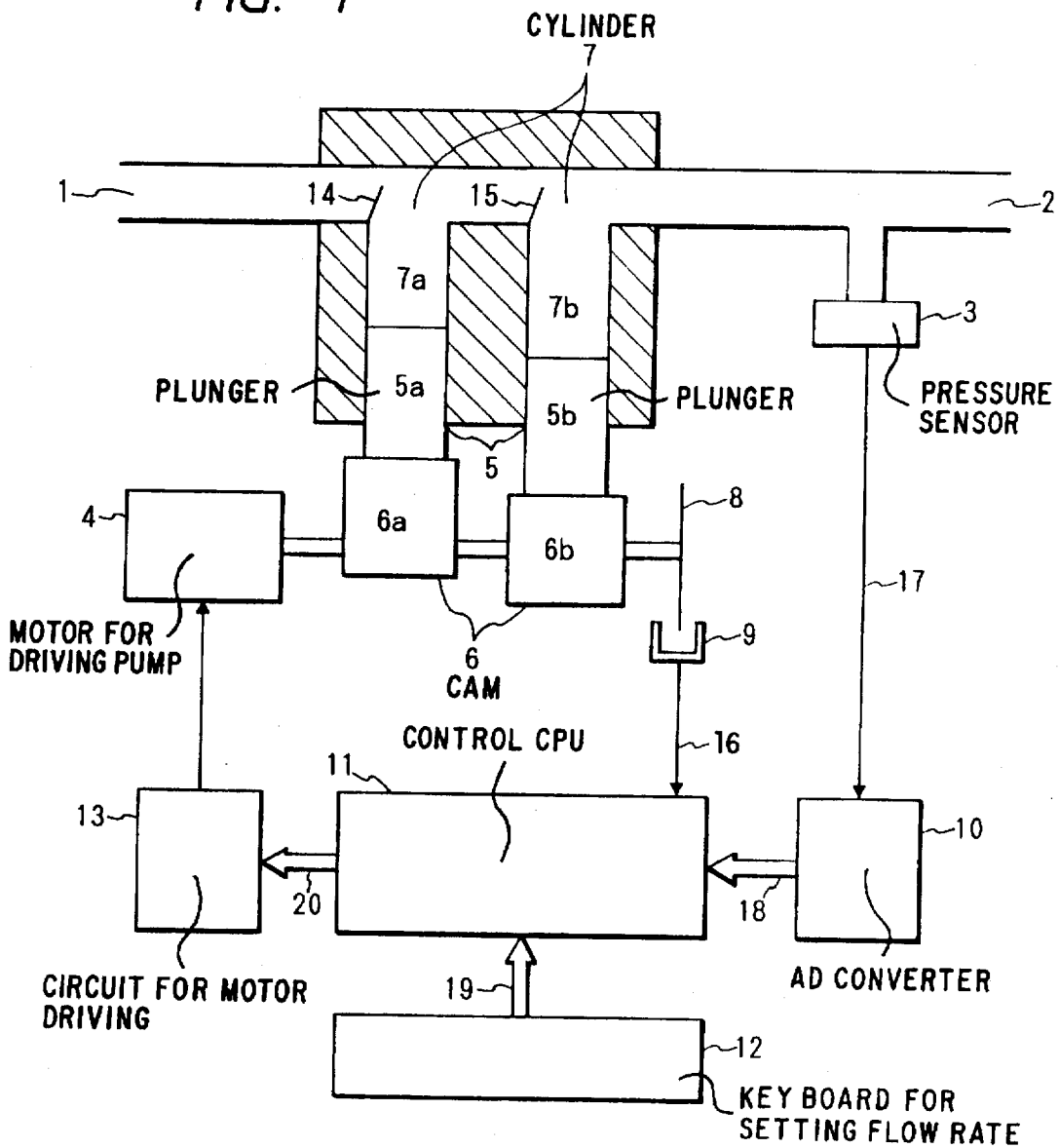
FIG. 1 is a drawing showing the hardware structure of the present invention.

In the construction according to the present invention, as first controlling means, there is provided means which has a local cam in such a shape that a certain period capable of measuring the pressure value of delivered liquid varying depending on the load is obtained during one cycle of the pump, and controls with the pressure measured during this period as a standard pressure value the delivery pressure value so as to always become the standard pressure value during the remaining period. The relationship among the flow rate of liquid F, the delivery pressure of liquid P and the resistance of liquid flow passage R is $F \propto P/R$, and one cycle time of the pump is sufficiently small comparing to the changing time of the resistance of liquid flow passage. Therefore, the control is performed alternatingly using pressure-priority controlling means for changing the rotating speed of motor for driving the pump and rotating-speed-priority controlling means during one cycle operation of the pump so as to absorb the fluctuation in the delivery pressure due to adjustment accuracy of cam, presence of bubbles and operating time lag of checking valves.

As second controlling means, there is provided means for automatically shifting a period measuring a standard pressure when a short-term pressure fluctuation due to presence of bubbles occurs during the period of measuring the standard pressure to measure an erroneous standard pressure value.

As third controlling means, there is provided means for automatically judging incapability of measuring a correct standard pressure when a long-term pressure fluctuation due to, for example, change of flow passage occurs during the period of measuring the standard pressure to execute a different control from the pressure-priority control.

It has been revealed from an experiment that it is possible to predict when the time of opening/closing operation of valve in the pump comes during one cycle operation and that the opening/closing operation of valve becomes fast and correct by instantaneously changing the flow of liquid at that time. Therewith, as fourth controlling means, there is provided means for instantaneously changing the rotating speed of the motor for driving the pump at that time.

It has been revealed that it is possible to predict when the time of opening/closing operation of valve in the pump comes during one cycle operation and that change in the delivery pressure of the pump occurs when the valve does not correctly operate. Therewith, further, as fifth controlling means, there is provided means for instantaneously changing the rotating speed of the motor for driving the pump when fluctuation occurs in the delivery pressure of the pump during the operation period of valve.

The rotating speed at which the motor for driving the pump should be rotate to deliver liquid at a required flow rate is determined as a design value of the pump. The rotating-speed-priority controlling means controls so as to give a higher priority to rotate the motor at the rotating speed determined by the design value, and not to change the rotating speed of motor even if pressure fluctuation within a pre-determined pressure range occurs. When a large pressure fluctuation exceeding the pre-determined pressure range occurs, the rotating speed of the motor is increased or decreased to, for example, twice or a half.

The pressure-priority controlling means functions such that the delivery pressure becomes always equal to a standard pressure value by control for increasing the rotating speed of the motor for driving the pump until the delivery pressure increases up to a pressure given as the standard pressure value, by control for decreasing the rotating speed of the motor for driving the pump until the delivery pressure decreases up to the standard pressure value and by control for keeping the rotating speed of the motor for driving the pump as it is when the standard pressure value is equal to the delivery pressure.

The operation of the standard pressure measuring means is different depending on its construction. In the case of the first controlling means described above, the standard pressure measuring means functions such as to read out a delivery pressure during a pre-determined period and transfer it as a standard pressure to the pressure-priority controlling means.

In the case of the second controlling means described above, the standard pressure measuring means functions such as to act as measuring period monitoring means for performing detection of change in the rotating speed of the motor for driving the pump during a pre-determined period, measuring period shifting means for shifting the measuring period depending on an instructions from the measuring period monitoring means, and signal averaging means for performing averaging processing of pressure data read out during the measuring period and for transferring it as a standard pressure value to the pressure-priority controlling means.

In the case of the third controlling means described above, the standard pressure measuring means functions such as to act as control method switching means for performing prohibition of pressure-priority control depending on an instruction from said measuring period monitoring means.

The operation of the valve operation correcting controlling means in the fourth controlling means is different from that in the fifth controlling means.

In the case of the fourth controlling means, the valve operation correcting controlling means functions such as to act as valve operation controlling means for performing instantaneous change of the rotating speed of the motor for driving the pump when the plunger of the pump comes to the opening/closing operating position of the valve.

In the case of the fifth controlling means described above, the valve operation correcting controlling means functions such as to act as valve operation controlling means for performing instantaneous change of the rotating speed of the motor for driving the pump when both conditions of the plunger of the pump coming to the opening/closing operating position of the valve and the occurrence of pressure fluctuation simultaneously occur. An embodiment according to the present invention will be described. The embodiment according to he present invention is composed of hardware showing in FIG. 1 and software showing in FIG. 2 to FIG. 10.

As shown in FIG. 1, the hardware comprises two cylinders 7, two plungers 5, two cams 6 to reciprocate each of the plungers in each of the cylinders, a motor 4 for driving the pump to rotate the two cams, a suction valve 14 to open only when liquid is sucked from a suction port 1 into the inside of the cylinder, a delivery valve 15 to open only when liquid is delivered from the cylinder 7a to the cylinder 7b, a chopper plate 8 to give signals to a cam position detector 9 during period from the time when the cam 6 comes to the position to initiate sucking liquid from the suction port 1 of the pump into the cylinder 7a to the time of completion of sucking. A pressure sensor 3 attached in a delivery port 2 of the pump always outputs an analog signal 17 of pressure indicating the delivery pressure of liquid. In the pump having the above construction, the delivery flow rate decreases when the rotating speed is decreased. The relationship among the resistance of liquid flow passage R connected to the delivery port of the pump, the delivery pressure of liquid P and the flow rate of liquid F is F α P/R.

An AD converter 10 receives the analog signal 17 of pressure, converts it to a digital signal 18 of pressure, and transmits it to a control CPU 11 for controlling the operation of the pump. The control CPU 11 receives set data 19 for flow rate from a key-board 12 for setting flow rate and an under-sucking signal 16 indicating an operation period of the pump from the initiation of sucking to the completion of sucking output from the cam position detector 9.

By inputting the data and signals, the control CPU 11 controls the flow rate of liquid by transmitting the data to determine the rotating speed of the motor.

The control operation of an embodiment of the control CPU 11 according to the present invention will be described below, referring to FIG. 2 to FIG. 10.

Figure 2:
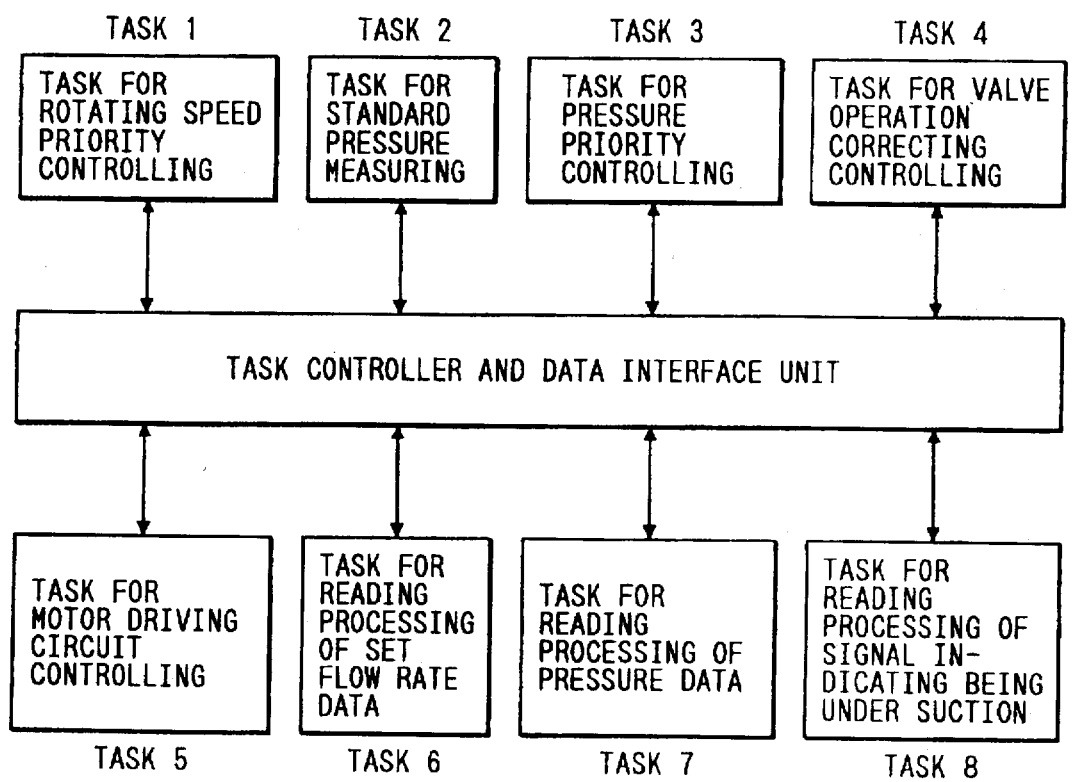
FIG. 2 is a diagram showing the software structure of the present invention.
Figure 3:
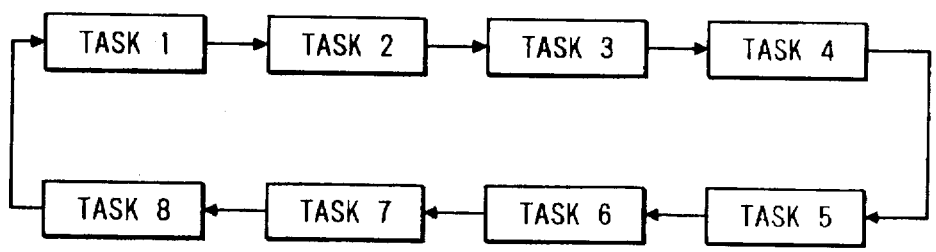
FIG. 3 is a diagram showing the task control operation of the present invention.

FIG. 2 shows a task controller and data interface unit to control operation of each controlling task and to interface between the tasks for data and timing signals. The task 1 to the task 8 are controlled by the task controller such that the programs of tasks are sequentially executed step by step as shown in FIG. 3.

Assuming that the time to execute one step in the each program is, for example, 100 nano-seconds, each of the programs is executed by one step every 800 nano-seconds. Even when the rotating speed of the motor for driving the pump is 10 rotations/second (one rotation in 100 milli-seconds) at the maximum, 125,000 steps of the programs can be executed during one rotation of the motor. Further, since number of steps composing one task is less than 100 steps at the maximum, one task can be executed 1250 times during one rotation of motor. This makes high response controlling possible.

The operation of each task will be described below. Task for motor driving circuit controlling receives set data for rotating speed of motor from another task, converting it into the set data 20 for rotating speed of motor by which a circuit for motor driving determines a rotating speed of motor, transferring it to the circuit for driving motor 13. Task for reading processing of set flow rate data converts a set flow rate from the key board 12 for setting flow rate into read-out flow rate data depending on the kinds and order of keys pushed in the key board, transferring it to the data interface unit. Task for reading processing of pressure data reads out pressure data 18 output from the AD converter 10 and transmits it to the data interface unit. Task for reading processing of signal indicating being-under-suction transmits signals indicating that the pump is sucking liquid and that the pump initiates sucking operation to the data interface unit.

The operations of Task 1 to 4 shown in FIG. 4 to FIG. 10 will be described below.

Figure 4:
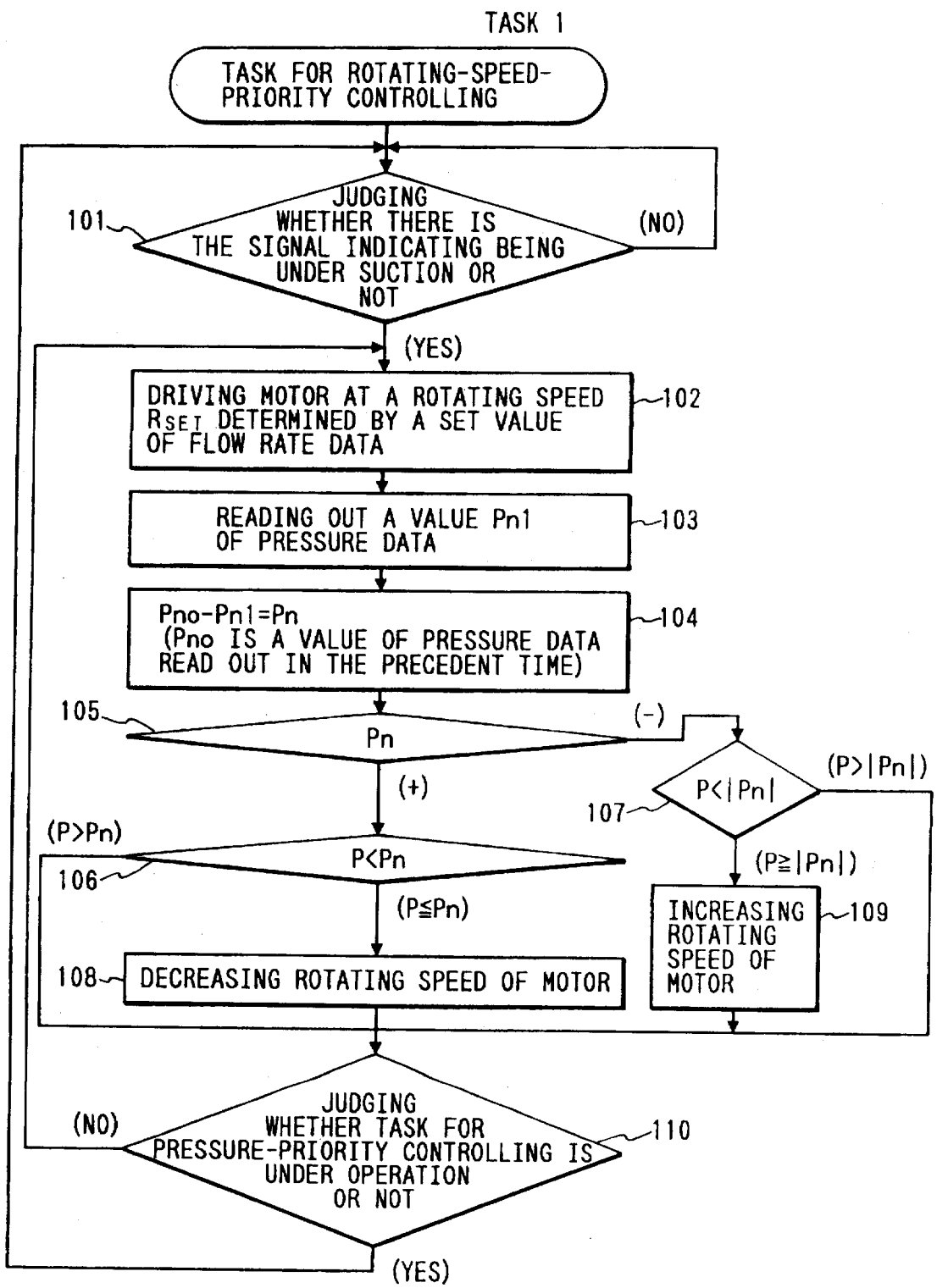
FIG. 4 is a flow chart showing a task for rotating-speed-priority controlling.

Task for rotating-speed priority controlling shown in the flow chart of FIG. 4 functions when it is judged in Step 101 that the pump is under sucking state or it is judged in Step 110 that Task for pressure-priority controlling is under operation. The task sets the rotating speed $R_{SET}$ determined by the set data for flow rate from Task for reading processing of set flow rate data in Step 102. However, as shown in Step 103 to Step 109, the rotating speed of motor is increased for a certain period only when the amount of fluctuation in pressure data exceeds a certain value. This is to correct the instantaneous fluctuation in flow rate due to presence of bubbles or operation lag of valve.

Figure 5:
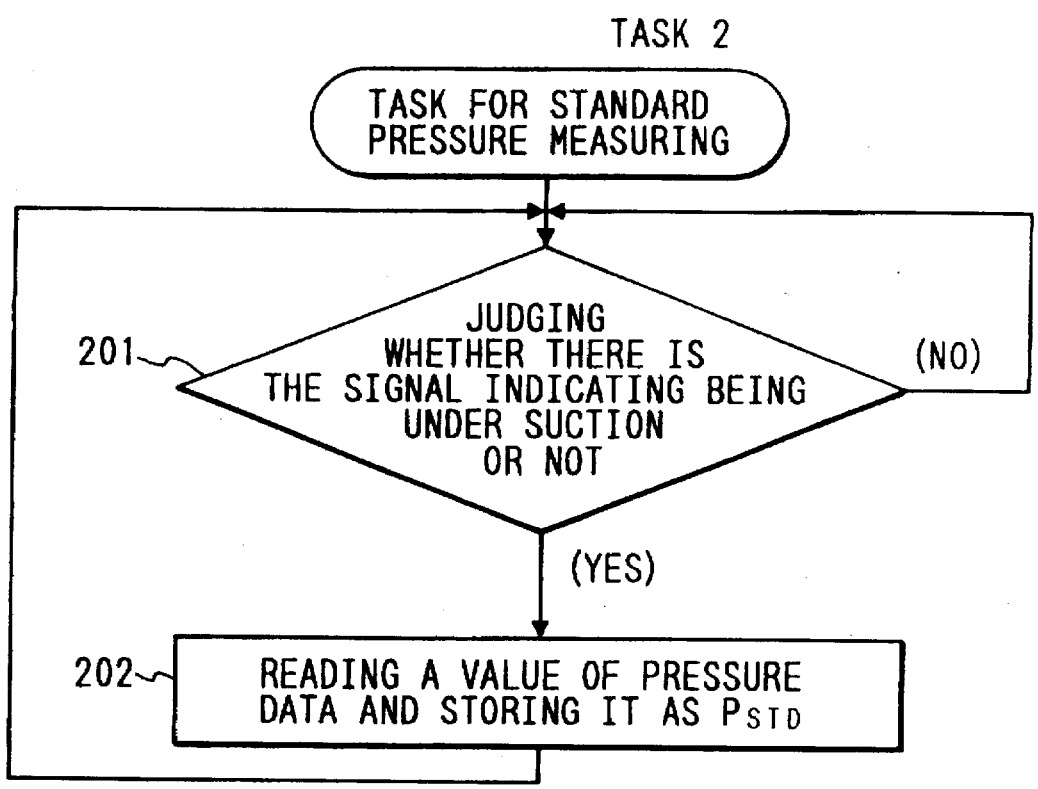
FIG. 5 is a first flow chart showing a task for standard pressure measuring.

Task for standard pressure measuring shown in the flow chart of FIG. 5 functions when it is judged in Step 201 that the pump is under sucking state. In Step 202, pressure data is read out and transmitted as a standard pressure value $P_{STD}$ to Task for pressure-priority controlling through the data interface unit.

Figure 6:
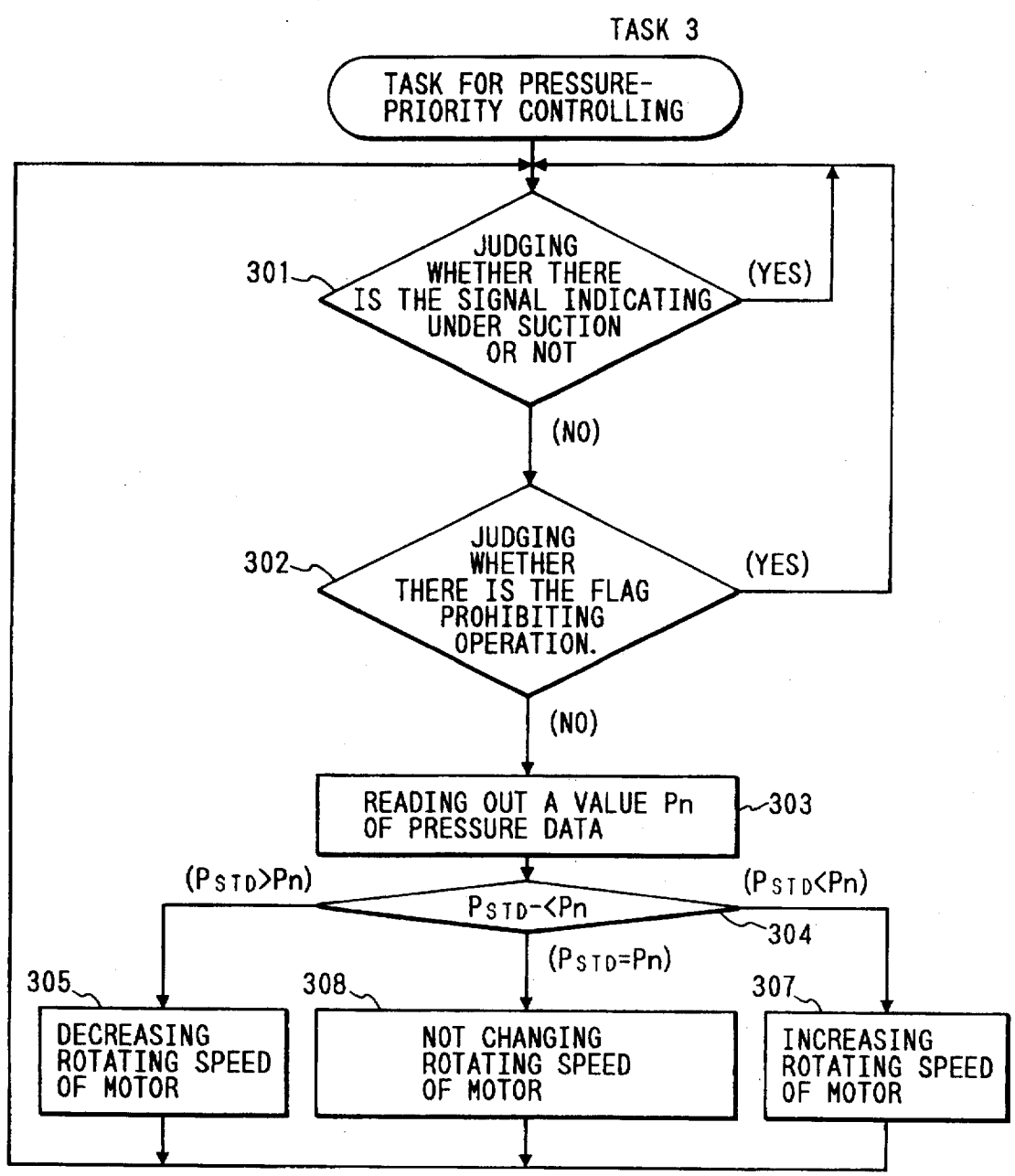
FIG. 6 is a flow chart showing a task for pressure-priority controlling.

Task for pressure-priority controlling shown in the flow chart of FIG. 6 functions when it is judged in Step 301 and Step 302 that the pump is not under sucking state and there is no flag prohibiting to operate this task. The operation of this task is to change the rotating speed of the motor in Steps 303 to 307 such that the pressure data value always becomes equal to the standard pressure value $P_{STD}$ transmitted from Task for standard pressure measuring.

Figure 9:
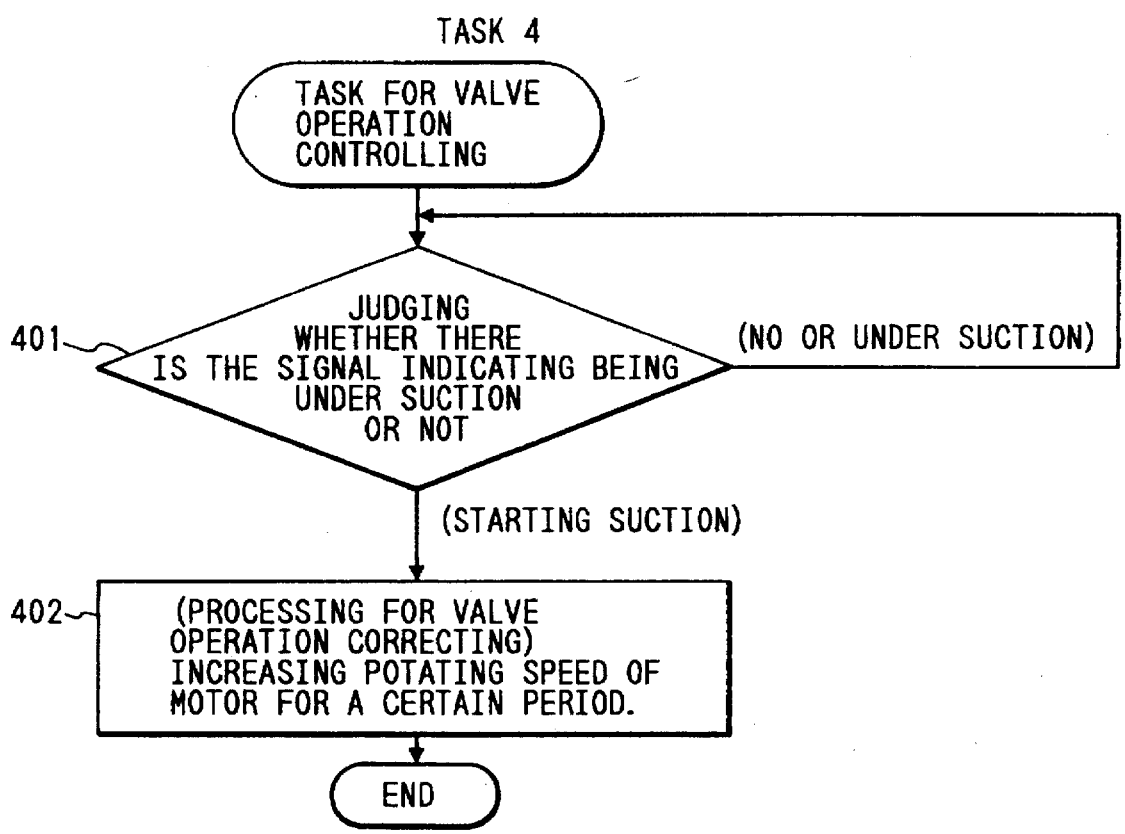
FIG. 9 is a flow chart showing a task for valve operation controlling.

Task for valve operation controlling shown in the flow chart of FIG. 9 functions when it is judged in Step 401 that the pump comes at the time to initiate sucking and in Step 402 instantaneously increases the rotating speed of the motor to accelerate opening of the suction valve and closing of the delivery valve in the pump. As described above, Tasks 1 to 4 function every cycle of the pump.

Figure 7:
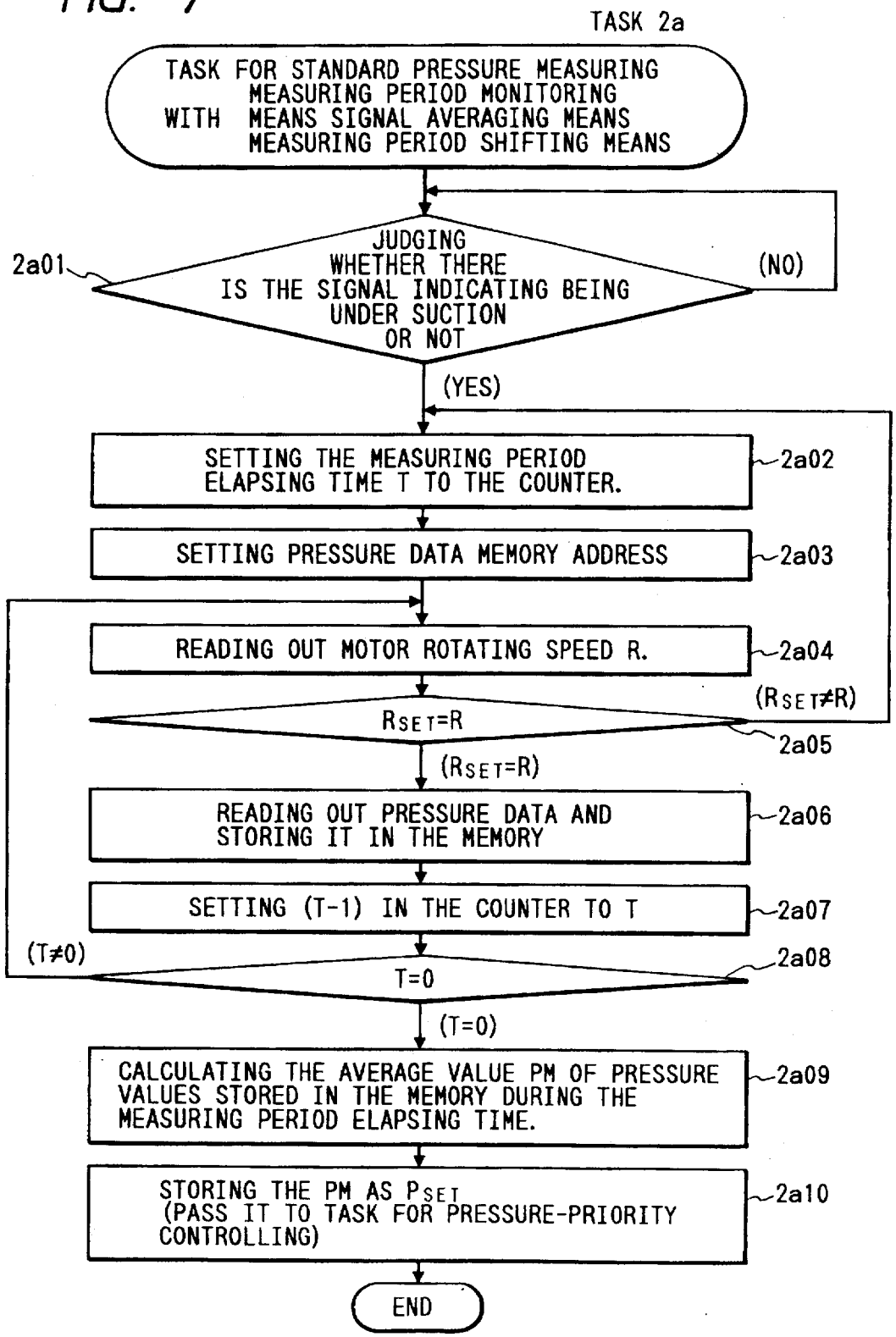
FIG. 7 is a second flow chart showing a task for standard pressure measuring.
Figure 8:
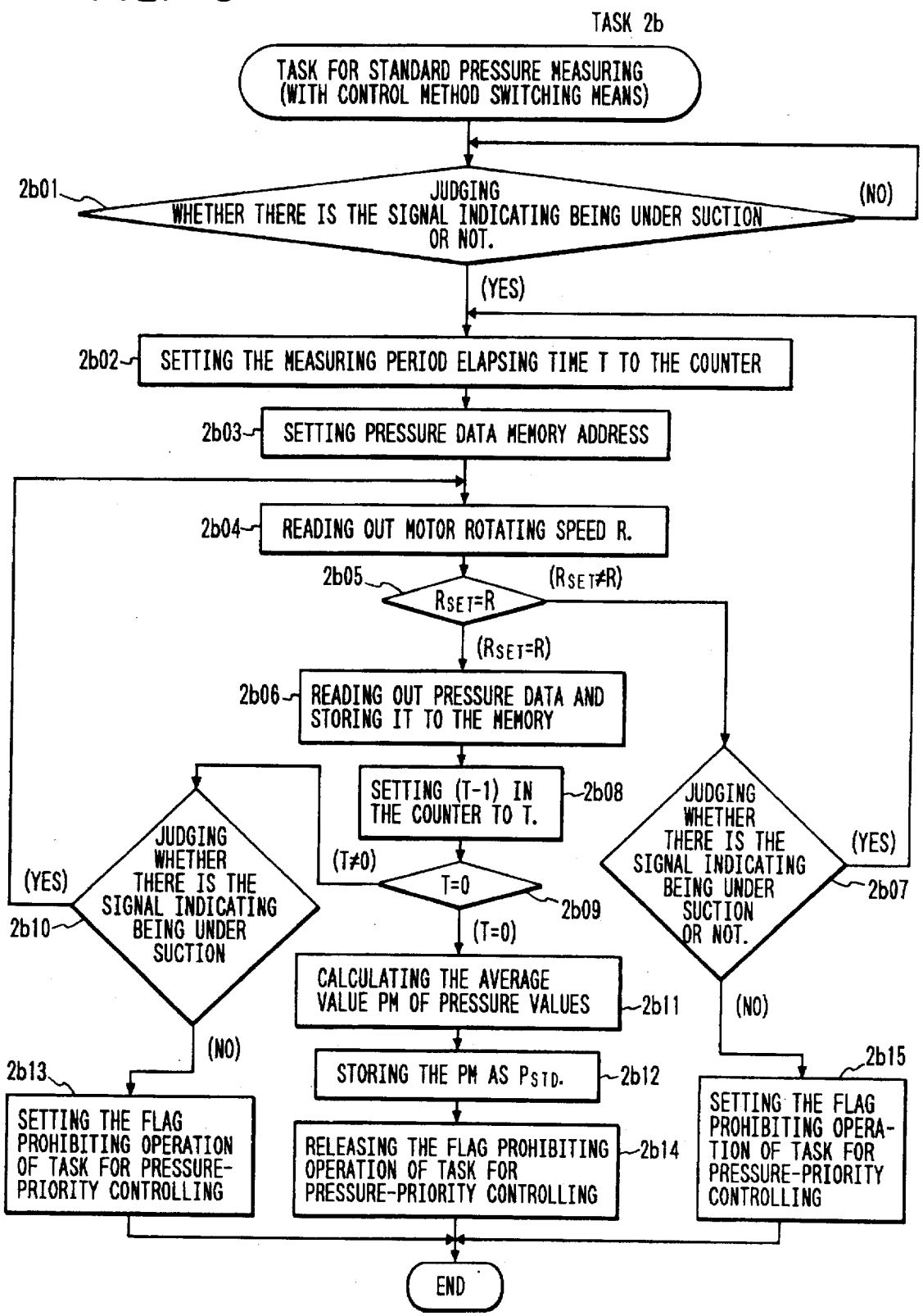
FIG. 8 is a third flow chart showing a task for standard pressure measuring.

The flow charts in FIG. 7 and FIG. 8 show two different embodiments of Tasks for standard pressure measuring. Task 2a for standard pressure measuring shown in FIG. 7 monitors in Steps 2a02 to 2a05 whether the rotating speed of the motor is changed during measuring the standard pressure and shift the measuring period when the rotating speed of the motor is changed. And further calculation is executed in Step 2a09 to obtain an average value of the pressure data obtained during the standard pressure measuring period, said average value is set as a standard pressure value.

Task for standard pressure measuring shown in FIG. 8 functions in Steps 2b02 to 2b05 when the standard pressure value is being measured and the measuring period is being shifted due to change in the rotating speed of the motor, detects in Steps 2b07 and 2b10 that the measuring is not completed even the completion of sucking operation of the pump and sets the flag prohibiting operation of Task for pressure-priority controlling. And when the measurement is completed in Step 2b14, the flag prohibiting operation of Task for pressure-priority controlling is released.

Figure 10:
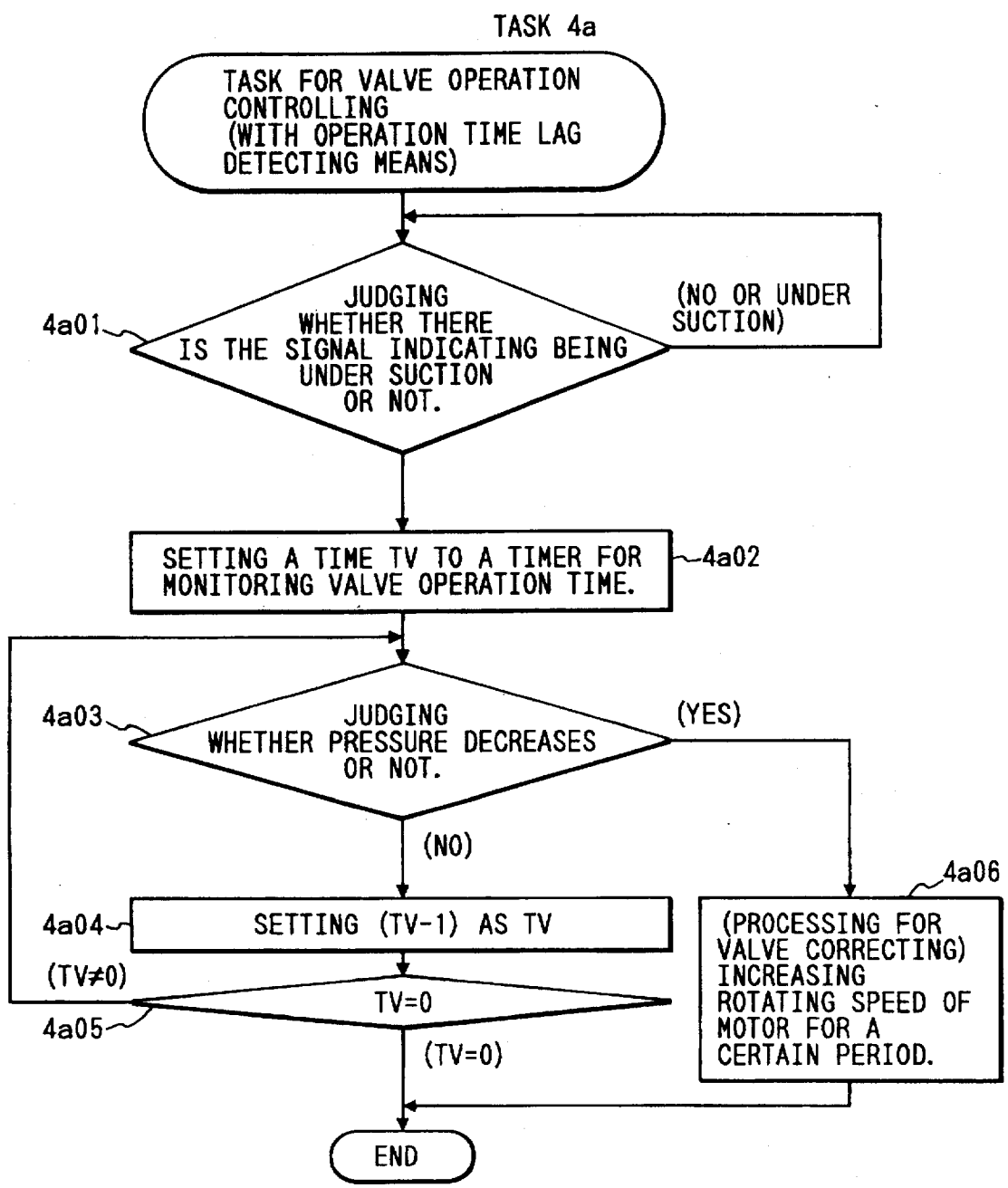
FIG. 10 is a second flow chart showing a task for valve operation controlling.

FIG. 10 is a flow chart showing another embodiment of a different task for valve operation controlling which performs operating correction processing for the valve in Steps 4a02 to 4a05 only when change in pressure occurs at the time of valve operation.

According to the embodiment shown in FIG. 1 to FIG. 6, it becomes possible to detect fluctuation in flow rate from fluctuation of pressure and rapidly control so as to correct the fluctuation in flow rate, and the amplitude of fluctuation can be decreased to one-tenth in the converted value of flow rate from pressure fluctuation as small as that with the conventional technology.

According to the embodiment in FIG. 7, it is possible to eliminate effect of trouble instantaneously occurring during measuring the standard pressure.

According to the embodiment in FIG. 8, it is possible to eliminate controlling error in flow rate control due to disturbance occurring during measuring the standard pressure.

According to the embodiment in FIG. 10, it is possible to eliminate instantaneous and small ripples due to valve operation correcting control occurring even when the valves normally operate.

According to the present invention, it is possible to attain the effect of substantially decreasing the fluctuation in flow rate such as fluctuation in flow rate due to the limitation of accuracy in the cams of pump, fluctuation in flow rate due to operating lag of the valves in pump, fluctuation in flow rate due to presence of bubbles entering into the pump or bubbles generated in the pump.

What is claimed is:

1. A precisely flow-controlling pump for delivering liquid through rotation of a pump driving motor, comprising:

a rotating device coupled to the rotating pump driving motor, wherein an operating cycle of the pump is periodically formed during a fixed number of rotations of the rotating device and said operating cycle comprises first and second periods of time;

a pressure detector detecting pressure of the delivered liquid during the first period of time; and a controller coupled to and controlling the pump driving motor wherein the pump driving motor rotates at a set rotating speed during the first period of time and the pressure of the delivered liquid is maintained constant by controlling the rotating speed of the pump driving motor on the basis of the detected pressure during the second period of time that the pump driving motor is rotated;

wherein, when the pressure detector detects that the liquid pressure is out of a predetermined pressure range during the first period of time, the controller controls the rotating device so as to change the rotating speed of the pump driving motor during the first period of time to thereby cause the detected pressure to fall within the predetermined pressure range.

2. A precisely flow-controlling pump for delivering liquid through rotation of a pump driving motor, comprising:

a rotating device coupled to the rotating pump driving motor, wherein an operating cycle of the pump is periodically formed during a fixed number of rotations of the rotating device add said operating cycle comprises first and second periods of time;

a pressure detector detecting pressure of the delivered liquid during the first period of time; and a controller coupled to and controlling the pump driving motor wherein the pump driving motor rotates at a set rotating speed during the first period of time and the pressure of the delivered liquid is maintained constant by comparing the detected, pressure with a predetermined value and controlling the rotating speed of the pump driving motor on the basis of the detected pressure during the second period of time while the pump driving motor is rotated;

wherein the controller monitors and averages the pressure of the delivered liquid while the rotating speed of the pump driving motor substantially coincides with the set rotating speed during the first period of time, and wherein the predetermined value equals the averaged pressure.

3. A precisely flow-controlling pump according to claim 2, wherein, if at anytime during-the first period the rotating speed of the pump driving motor does not substantially coincide with the set-speed, the controller averages the pressure of the delivered liquid only after the rotating speed of the pump driving motor comes to coincide with the set rotating-speed.

4. A precisely flow-controlling pump according to claim 2, wherein, if at any time during the first period the rotating speed of the pump driving motor does not substantially coincide with the set speed, the controller stops controlling the rotating means so as to control the rotating speed of the pump driving motor during the remaining period of time to thereby maintain the pressure of the delivered liquid constant.

5. A precisely flow-controlling pump, comprising:

first and second plunger pumps serving to suck and deliver liquid, the first and second plunger pumps having first and second plungers, respectively;

suction and delivery valves which are associated with the first and second plunger pumps so that the suction valve is open and the delivery valve is closed when the first plunger pump sucks the liquid and the suction valve is closed and the delivery valve is open when the first plunger pump delivers the sucked liquid;

a cam mechanism driving the first and second plungers of the first and second plunger pumps so as to deliver the sucked and delivered liquid by the first plunger pump to thereby make substantially constant a flow rate of the liquid delivered from an outlet of the second plunger pump by a combination of the first and second plunger pumps, wherein an operating cycle of the pump is periodically formed during a fixed number of rotations of said cam mechanism and said operating cycle consists of first and second periods of time;

a motor for driving the cam mechanism;

a pressure detector detecting pressure of the liquid delivered from the outlet of the second plunger pump during the first period of time; and a controller coupled to and controlling the motor wherein the motor rotates at a set rotating speed during the first period of time and the pressure of the delivered liquid from the outlet of the second plunger pump is maintained constant by controlling the rotating speed of the motor on the basis of the detected pressure during the second period of time.

6. A precisely flow-controlling pump according to claim 5, wherein the first plunger pump sucks the liquid during the first period of time.

7. A precisely flow-controlling pump according to claim 5, wherein the controller predicts operation timings of the first and second valves to change the rotating speed of the motor.

8. A precisely flow-controlling pump according to claim 5, wherein the controller changes the rotating speed of the motor when fluctuation in the pressure of the delivered liquid from the second plunger pump occurs within an operation period of the first and second valves predicted from operation timings of the pump.

9. A precisely flow-controlling pump for pumping liquid comprising:

a rotating motor that rotates a cam mechanism, wherein a fixed number of rotations of said cam mechanism is an operating cycle of the pump;

a pumping mechanism driven by said motor and said cam mechanism, wherein said pumping mechanism pumps the liquid from a source and outputs it to a delivery port;

a pressure sensor that measures the pressure of the liquid output from said delivery port;

a controller that controls the rotating speed of said motor and is connected to said pressure sensor, wherein said controller operates in a speed-priority mode during which the speed of the motor is held at a set rotating speed when the measured pressure is within a present range to determine a standard pressure, and a pressure-priority mode during which the speed of the motor is controlled so that the measured pressure equals said standard pressure;

wherein during a single operating cycle of the pump, said controller alternates between said speed-priority mode and said pressure-priority mode.

10. The precisely flow-controlling pump of claim 9, wherein said pump mechanism comprises a plurality of valves, and said valves are controlled by said controller so that said liquid is pumped from said source only during said speed-priority mode.

11. The precisely flow-controlling pump of claim 10, said pump mechanism further comprises:

a plurality of cylinders; and a plurality of plungers that reciprocate in said cylinders.

* * * * *

UNITED STATES PATENT AND TRADEMARK OFFICE
CERTIFICATE OF CORRECTION

PATENT NO. : 5,664,937
DATED : Sept. 9, 1997
INVENTOR(S) : Kenichiro TAKAHASHI et al.

It is certified that error appears in the above-identified patent and that said Letters Patent is hereby corrected as shown below:

| Column | Line |  |
|--------|------|--|
| 3 | 61 | Change "he" to --the--. |
| 6 | 46 | Change "add" to --and--. |
| 6 | 55 | After "detected" delete ",". |
| 6 | 67 | Change "during-the" to --during the--. |
| 7 | 2 | Change "set-speed" to --set speed--. |
| 7 | 5 | Change "rotating-speed" to --rotating speed--. |
| 8 | 29 | Change "present" to --preset--. |
| 8 | 45 | After "and" start new paragraph. |

Signed and Sealed this

Seventeenth Day of February, 1998

Attest:

BRUCE LEHMAN

*Attesting Officer*         *Commissioner of Patents and Trademarks*